(12) United States Patent
Hegeman et al.

(10) Patent No.: US 9,739,730 B2
(45) Date of Patent: Aug. 22, 2017

(54) QUANTITATIVE X-RAY ANALYSIS—MULTI OPTICAL PATH INSTRUMENT

(71) Applicant: PANalytical B.V., Almelo (NL)

(72) Inventors: Petronella Emerentiana Hegeman, Almelo (NL); Gustaaf Christian Brons, Almelo (NL); Aleksandr Komelkov, Almelo (NL); Bruno A. R. Vrebos, Almelo (NL); Waltherus Van Den Hoogenhof, Almelo (NL); Charalampos Zarkadas, Almelo (NL)

(73) Assignee: PANALYTICAL B.V., Almelo (NL)

( * ) Notice: Subject to any disclaimer, the term of this patent is extended or adjusted under 35 U.S.C. 154(b) by 205 days.

(21) Appl. No.: 14/637,833

(22) Filed: Mar. 4, 2015

(65) Prior Publication Data
US 2016/0258892 A1 Sep. 8, 2016

Related U.S. Application Data

(60) Provisional application No. 62/127,591, filed on Mar. 3, 2015.

(51) Int. Cl.
*G01N 23/22* (2006.01)
*G01N 23/223* (2006.01)

(52) U.S. Cl.
CPC ................. *G01N 23/223* (2013.01)

(58) Field of Classification Search
CPC ........... G01N 23/2204; G01N 23/2208; G01N 23/223
See application file for complete search history.

(56) References Cited

U.S. PATENT DOCUMENTS

| 6,285,734 B1* | 9/2001 | von Alfthan | G01N 23/223 378/22 |
| 6,292,532 B1* | 9/2001 | Kawahara | G01N 23/223 378/45 |
| 6,324,251 B1* | 11/2001 | Kuwabara | G01N 23/223 378/207 |
| 7,197,110 B2* | 3/2007 | Riess | G01N 23/06 378/45 |

(Continued)

FOREIGN PATENT DOCUMENTS

| JP | 02047542 A | * | 2/1990 |
| JP | H02 47542 | | 2/1990 |

OTHER PUBLICATIONS

English Translation of JP 02047542 A.*

*Primary Examiner* — David J Makiya
*Assistant Examiner* — Soorena Kefayati
(74) *Attorney, Agent, or Firm* — Leason Ellis LLP

(57) ABSTRACT

Apparatus includes an X-ray source 10, a wavelength dispersive X-ray detector for measuring X-ray fluorescence (XRF) and an energy dispersive X-ray detector 14 again for measuring X-ray fluorescence. Selected elements are measured using the wavelength dispersive process to reduce the overall measurement time compared with using only one of the two detectors or compared to a simple approach of measuring low atomic number elements with the wavelength dispersive detector and high atomic number elements with the energy dispersive detector. The selection can take place dynamically, in particular on the basis of the results of the energy-dispersive detector.

18 Claims, 4 Drawing Sheets

(56) References Cited

U.S. PATENT DOCUMENTS

| | | | | |
|---|---|---|---|---|
| 7,424,093 B2* | 9/2008 | Fukai | G01N 23/223 378/208 |
| 7,592,591 B2* | 9/2009 | Notoya | G01N 23/22 250/306 |
| 7,796,726 B1* | 9/2010 | Gendreau | G01N 23/20 378/44 |
| 7,916,834 B2* | 3/2011 | Piorek | G01N 23/223 378/102 |
| 8,223,925 B2* | 7/2012 | Shannon, Jr. | G01N 23/223 378/147 |
| 8,891,729 B2* | 11/2014 | Matoba | G01N 23/223 378/46 |
| 9,377,419 B2* | 6/2016 | Las Navas Garcia | G01N 5/045 |
| 9,449,780 B2* | 9/2016 | Chen | H01J 35/08 |
| 2008/0310587 A1* | 12/2008 | Hegeman | G01N 23/223 378/44 |

\* cited by examiner

QUANTITATIVE X-RAY ANALYSIS—MULTI OPTICAL PATH INSTRUMENT

CROSS-REFERENCE TO RELATED APPLICATIONS

This application is based on and claims priority to U.S. Provisional Patent Application Ser. No. 62/127,591, filed on Mar. 3, 2015, which is hereby incorporated by reference as if set forth in its entirety herein.

FIELD OF INVENTION

The invention relates to a method of quantitative X-ray analysis and apparatus for carrying out the method.

BACKGROUND TO THE INVENTION

Materials analysis using X-rays provides accurate data in a number of applications and industries. X-ray fluorescence (XRF) measurements allow the determination of the elemental composition of a sample. This may be carried out in dedicated X-ray fluorescence apparatus with an X-ray source, an X-ray detector and a sample stage for holding a sample.

In order to make an XRF measurement it is necessary to measure the intensity of X-rays at a particular wavelength, equivalently energy, excited in a sample by the incident X-ray beam. In the case of energy dispersive XRF, an energy dispersive detector is used, i.e. a detector that measures the X-ray intensity as a function of energy. However, for high accuracy, especially where the emission lines of different elements are close in energy and even overlapping, this approach may not provide enough energy resolution. In this case, in an alternative approach, wavelength selective XRF is used. In this alternative approach, a wavelength selecting crystal is provided between the sample stage and the X-ray detector to select only a particular wavelength for measurement by the X-ray detector.

High accuracy XRF apparatus typically mount the wavelength selecting crystal and X-ray detector on a goniometer to allow the wavelength selecting crystal and X-ray detector to be moved to different positions to select different wavelengths. Where it is necessary to measure a sample with multiple components, each component is measured in turn before realigning the wavelength selecting crystal and X-ray detector for the next measurement.

The length of time to make a measurement of a single component varies as a result of a number of factors, including how much of a component is present in a sample and the desired accuracy. However, in general, it may be said that accurately measuring a large number of components in a sample may take a considerable time, especially where some of the components are trace components present in small quantities.

This time taken for measurement can be a particular concern in some industrial applications. For example, where the XRF measurement is intended to check the composition of steel, it may be necessary to pause the production process while the measurement is being made before releasing the molten metal to the next stage of a process. This can cost a considerable amount of resource in maintaining the temperature above the melting temperature. Similarly, in a mining application, it may again be necessary to evaluate the material being extracted from the earth rapidly.

In an existing solution to this problem, a large number of different X-ray detectors are each used, each aligned with a fixed wavelength selecting crystal to measure a particular wavelength and hence a particular element. This allows measurements to be made in parallel. However, such equipment is not suitable in cost-sensitive applications since there is a need for a large number of X-ray components.

Energy dispersive XRF measures X-ray intensity as a function of energy and measures a number of elements simultaneously. Its performance is very good for transition metals. For low atomic number its sensitivity is poor compared to WDS. For the high energy of high atomic number elements the efficiency of the detector is low for thin Si body detectors (~500 um), the X-rays may pass through the detector with little interaction, so energy dispersive XRF may also be unsuitable at very high energies.

There therefore remains a need for speeding up the measurement of the composition of a sample using XRF.

SUMMARY OF THE INVENTION

In a first aspect of the invention, there is provided a method of quantitative X-ray fluorescence, XRF, analysis of a sample of a specified type to measure the concentration of a plurality of elements in respective concentration ranges, the method comprising:

carrying out energy dispersive XRF, ED-XRF, to measure the concentration of a selected first subset of the predetermined elements;

carrying out wavelength dispersive XRF, WD-XRF, to measure the concentration of a selected second sub-set of the elements;

wherein the elements are divided between the first and second subsets according to a criterion to deliver a reduced overall measurement time to measure all the plurality of elements to a given accuracy and/or precision compared to using only one of the energy dispersive XRF and the wavelength dispersive XRF.

By selecting elements for measurement using WD-XRF and ED-XRF the total overall measurement time may be reduced for a given accuracy and/or precision.

The given accuracy and/or precision may be predetermined. Alternatively, the total measurement time may be predetermined and the precision of the measurements improved as much as possible given the measurement time. Either way, the measurement time is shorter combining the WD-XRF and ED-XRF than it would be measuring all elements by the same one of WD-XRF and ED-XRF to the same precision and accuracy.

Precision is preferably the most important factor, i.e. the repeatability of the measurement. Accuracy may also be a constraint though it is less critical and is less determined by the method—for example sample preparation may be relevant for accuracy. The skilled person may also consider a required Lower Limit of Detection, LLD as a constraint in the criterion for reducing measurement time.

Note that the criterion is preferably not simply dividing the elements by atomic number but preferably more sophisticated division is used to improve results.

Thus, the criterion preferably reduces measurement time compared with a simplistic method of dividing elements simply depending on their atomic number.

Thus, the method may include dividing the elements between the first and second subsets according to a criterion to reduce the overall measurement time to measure all the plurality of elements to a predetermined precision, and/or accuracy and/or LLD compared to a method using WD-XRF for all elements up to a predetermined atomic number and ED-XRF for all elements with a higher atomic number.

Note that the inventors have realised that ED-XRF may be suitable also for higher atomic numbers since the problem with conventional ED-XRF for high atomic number are a result of the low power used in conventional XRF equipment using ED-XRF. By providing a suitable X-ray source for WD-XRF of higher power than normally used for ED-XRF, the fact that a significant percentage of X-rays pass through the ED-XRF detector is not a problem since with a high power X-ray source there is more than enough intensity at the ED-XRF detector even if only a small percentage of the X-rays interact with the detector.

In a preferred embodiment, the criterion uses the reciprocal sensitivity of measurement E of each element by ED-XRF and WD-XRF. This provides a key measure of intensity per unit time allowing for the optimisation and reduction of measurement time.

The criterion for each element may further takes into account the overlaps of other peaks, the expected concentration ranges and/or backgrounds of the predetermined elements.

In the case that condition that the peak from the element is much higher than the background, the condition for ED-XRF to be used instead of WD-XRF may be given by:

$$\frac{E_{ED}}{E_{WD}} \leq \frac{t_{ED}}{t_{WD}} \quad (1)$$

where E is the reciprocal of the sensitivity, $E_{ED}$ is the reciprocal sensitivity for ED-XRF, $E_{WD}$ is the reciprocal sensitivity for WD-XRF, $t_{ED}$ is the measurement time for the ED-XRF measurements and $t_{WD}$ is the measurement time for the WD-XRF measurement. This is to compare the total count in the ED and WD channel and select the ED channel where there are sufficient counts.

In the case that condition that the peak from the element is not much higher than the background, the counting statistical error (CSE) needs to be compared not the counts. Accorignly the condition for ED-XRF to be used instead of WD-XRF may be given by:

$$E_{WD}\sqrt{\frac{r_{peak}}{t_{peak}} + l_{bkg1}^2 \frac{r_{blg1}}{t_{bkg1}} + l_{bkg2}^2 \frac{r_{bkg2}}{t_{bkg2}} + \ldots} \geq \quad (2)$$

$$E_{ED}\sqrt{\frac{1}{LT} \cdot \left(\frac{r_{peak}}{t_{ED}} + \frac{r_{bkg}}{t_{ED}}\right)}$$

where $r_{peak}$ is the count rate at the peak position, $t_{peak}$ is the measurement time of the peak, $r_{bkg1}$ is the count rate at the $1^{st}$ background position, $t_{bkg1}$ is the measurement time of background1, idem background position 2, $l_{bkg}$ is the background factor, LT is the Live Time of the ED channel in relative units, $r_{peak}$ the count rate at the peak position, $r_{bkg}$ is the count rate at the background position, and $t_{ED}$ is the measurement time of the ED channel.

The quantity in square roots is the CSE and the E the inverse sensitivity and the whole formula estimates the spread in determined concentration for the WD channel (left side of equation) and for the ED channel (right side of equation). This gives a measure of the repeatability of the measurements in these two channels.

In embodiments, the ED-XRF measurements are carried out at the same time as at least some of the WD-XRF measurements. This may be done in particular where this reduces the total overall measurement time.

Alternatively, the ED-XRF measurements may be carried out before subsequently carrying out the WD-XRF measurements.

The method may include in particular determining dynamically which elements are to be measured by WD-XRF on the basis of the measurement results obtained by ED-XRF.

The method may further include carrying out the energy dispersive XRF measurements with the sample in a first measurement position and carrying out the wavelength dispersive XRF measurements with the sample in a second position.

The method may further comprise loading a sample onto the sample stage in the first position while carrying out the WD XRF measurements on another sample in the second position.

In another aspect, the invention relates to apparatus for carrying out X-ray fluorescence analysis comprising
a sample stage for carrying a sample;
an X-ray source arranged to direct X-rays to a sample on the sample stage;
a wavelength dispersive X-ray sensor;
an analyser crystal, wherein the analyser crystal cooperates with the wavelength dispersive X-ray sensor to direct X-rays of a selected wavelength emitted by the sample on the sample stage to the wavelength dispersive X-ray detector for measurement; and
an energy-dispersive X-ray detector;
further comprising a controller adapted to cause the apparatus to carry out a method as set out above.

Such apparatus is capable of carrying out improved XRF measurements by selecting appropriate elements for measurement by WD-XRF and ED-XRF.

The sample stage may be a movable sample stage having a first measurement position and a second measurement position;
wherein the X-ray source is arranged to direct X-rays to a sample mounted on the sample stage in the second measurement position;
the wavelength dispersive X-ray detector and analyser crystal are arranged to measure X-rays emitted by the sample in the second measurement position;
the apparatus further comprising a second X-ray source, arranged to direct X-rays to a sample mounted on the sample stage in the first measurement position;
wherein the energy-dispersive X-ray detector is arranged to measure the intensity of X-rays emitted by a sample in the first measurement position.

The sample stage may in particular be a rotary sample stage arranged to rotate to bring the samples between the first and second measurement positions.

By providing multiple measurement positions the measurement may be optimally speeded up.

The apparatus may further include a sample loader arranged to load a sample onto the sample stage in the first measurement position.

The second source may be a low energy X-ray source having a power of 5 W to 100 W, preferably 9 W to 50 W.

A collimator may be provided between the sample stage and the energy-dispersive X-ray detector.

The collimator may be a variable collimator with a plurality of settings, with at least one setting for reducing the intensity of X-ray radiation reaching the energy dispersive X-ray detector and at least one setting for reducing the detected spot size on the sample.

A filter of brass, Al, Ag, Cu or Be may be provided between the sample and the ED-XRF detector.

BRIEF DESCRIPTION OF THE DRAWINGS

An example of the invention will now be described with reference to the accompanying diagrams, in which.

DETAILED DESCRIPTION

Figure 1:
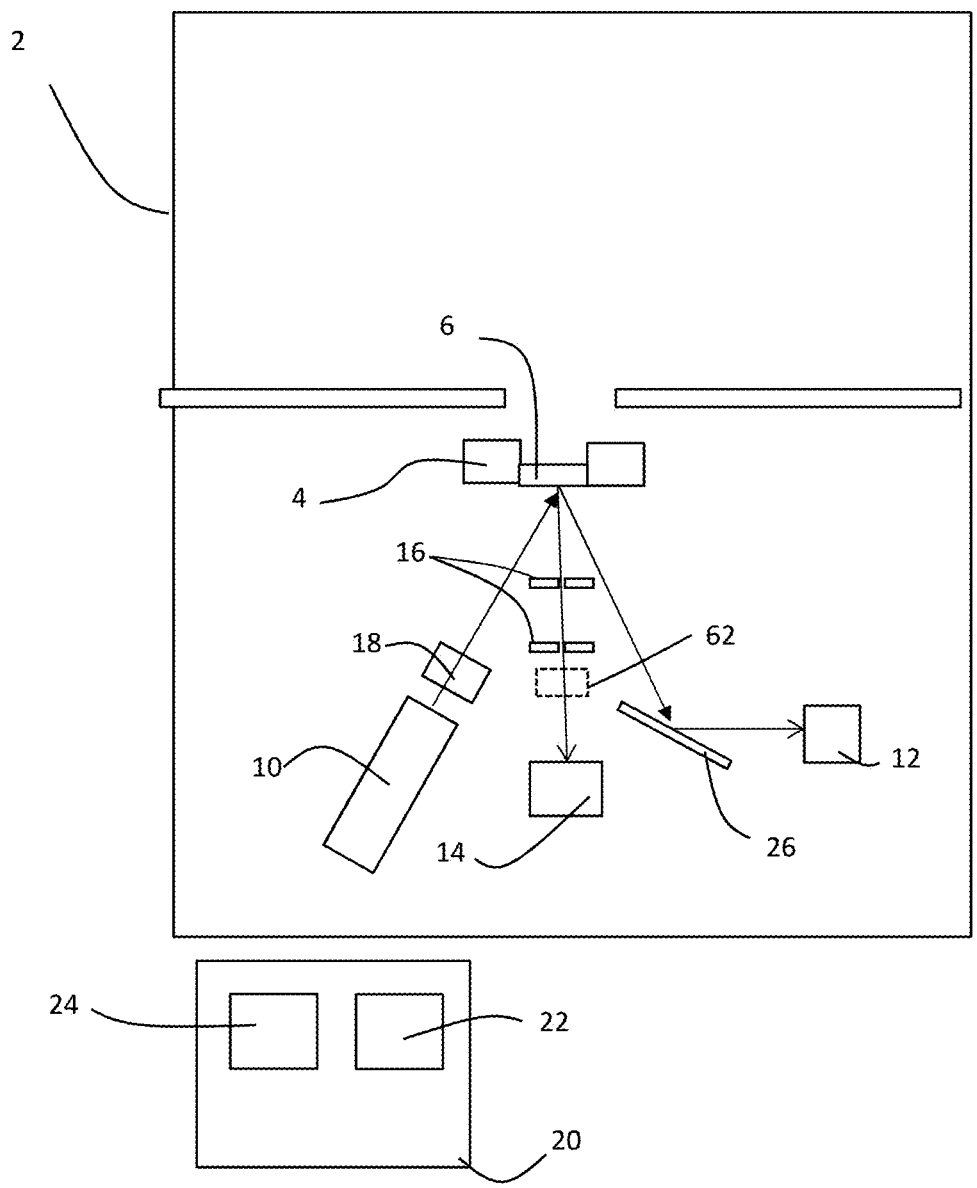
FIG. 1 shows a schematic of apparatus according to a first embodiment of the invention.

The invention relates to a method and apparatus for determining the elemental composition of a sample with multiple elements relatively quickly.

An X-ray apparatus 2 has a sample stage 4 for holding a sample 6. The upper part of the apparatus 2 is used for sample loading.

In practice, this apparatus 2 is a conventional XRF apparatus with an X-ray source 10 is mounted below the sample stage 4. In this embodiment there is a wavelength dispersive X-ray detector 12 for measuring X-ray fluorescence below the sample stage 4. The wavelength dispersive X-ray detector has an analyser crystal 26 for selecting X-rays only of a particular wavelength and an X-ray detector. The analyser crystal 26 and wavelength dispersive X-ray detector 12 are movable to allow selection of different wavelengths. Typically, the analyser crystal may be made of LiF, for example.

Additionally, an energy dispersive X-ray detector 14 is also mounted below the sample stage 4 to measure an X-ray spectrum, i.e. measured X-ray intensity as a function of X-ray energy. The energy dispersive detector may be, for example, a Silicon drift detector.

A number of other components are provided, including collimator 16 and filter 18. The filter may be omitted if not required. In the specific arrangement illustrated, the X-ray source 10 is a Rh tube and Al or brass filters 18 were used.

The collimator 16 is on the ED channel, i.e. between the sample stage and the energy dispersive X-ray detector 14, and may select a spot on the sample or control the X-ray flux as discussed in more detail below. The collimator shown is a double pinhole but in some applications a single pinhole or even a larger hole may be used instead.

The apparatus is under control of controller 20 which includes a memory 22 and processor 24.

In a first stage of measurement, the X-rays source is activated (by removing a shutter) and X-rays are incident on a sample. In this case, energy dispersive XRF measurements are made by the energy dispersive X-ray detector 14.

Then, wavelength dispersive X-ray measurements are made by the wavelength dispersive X-ray detector 12.

In order to speed up measurement, and to achieve high accuracy, it is important to correctly select which measurements are to be made with wavelength dispersive XRF (WD-XRF) and which are to be made with ED-XRF. This selection needs to be taken with a view to minimising total measurement time, while maintaining the required accuracy, taking into account the expected concentrations of various elements. This is particularly important for measuring trace elements, since the low intensity of X-rays emitted from trace elements typically requires long measurement times to collect sufficient X-ray photons for high accuracy.

Instead of targeting a particular accuracy, it is also possible to target a particular measurement time and seek to achieve the highest possible accuracy in that time.

One consideration is the atomic number Z of the element concerned. For elements with lower atomic numbers for example Mo, in general, WD-XRF is required, whereas for higher atomic numbers, such as for example Sn, ED-XRF can be better.

However, this is not always the case and simply selecting elements for measurement by the two methods does not always work. In particular, in the case that peaks for two elements lie close together, WD-XRF may be the only approach that can separate the peaks. Moreover, other considerations apply.

The method will be further explained using the example of the measurement of iron ore for clarity. It should be remembered however that the method is not restricted to the measurement of iron ore and a similar approach can be used for other samples.

TABLE 1

| Atomic number | ISO 9516 | EU Standard | Very important | Calibration range of oxides |
|---|---|---|---|---|
| 11 | | Na | Na | |
| 12 | Mg | Mg | Mg | 0.33-3.3 |
| 13 | Al | Al | | 0.19-6.6 |
| 14 | Si | Si | Si | 0.43-13.9 |
| 15 | P | P | P | 0.014-1.37 |
| 16 | S | S | S | 0.017-1.5 |
| 19 | K | K | K | 0.010-0.54 |
| 20 | Ca | Ca | Ca | 0.027-17.8 |
| 22 | Ti | Ti | | 0.027-7.8 |
| 23 | V | V | | 0.003-0.54 |
| 24 | Cr | Cr | | 0.009-0.035 |
| 25 | Mn | Mn | | 0.028-1.14 |
| 26 | Fe | Fe | | 54-102 |
| 27 | Co | | | |
| 28 | Ni | Ni | | 0.014-0.017 |
| 29 | Cu | Cu | | 0.015-0.076 |
| 30 | Zn | Zn | | 0.006-0.21 |
| 33 | As | As | | 0.011-0.079 |
| 50 | Sn | | | |
| 56 | Ba | | | |
| 82 | Pb | Pb | | 0.019-0.34 |

This table lists the elements of interest to be measured in this application with their atomic number, as well as the elements required by ISO 9516, standards, elements seen as very important, and the calibration range of oxides, i.e. the range of values of amounts (in %) of the respective oxides over which the measurements are to be calibrated. It will be seen that the calibration for examples requires Iron oxide to be measured up to 100% and that some other elements may be present in very small quantities.

Experiments were carried out under WD XRF for measurement times of 50 minutes, 15 minutes and 5 minutes using optimal conditions. Since the WD XRF measurements are carried out sequentially, the tube output voltage and current can both be varied for each measurement. For example, some materials may use a 25 kV source voltage and 160 mA current, while for others a higher source voltage of 50 kV but a lower current of 80 mA may be preferable.

Experiments were also carried out for the use of ED XRF. These measurements are carried out for all elements together, so it is not possible to vary the X-ray source voltage and current for each element. The experiments were carried out with the following combinations of voltage, current and times.

TABLE 2

| | kV/mA | Times (seconds) | Filter |
|---|---|---|---|
| 1 | 25/160 | 200/50/20 | |
| 2 | 32/125 | 200/50/20 | |
| 3 | 50/80 | 200/50/20 | |
| 4 | 60/66 | 150/38/16 | |
| 5 | 50/80 | 100/26/10 | Al-750 |
| 6 | 60/66 | 100/26/10 | Brass-400 |

Figure 2:
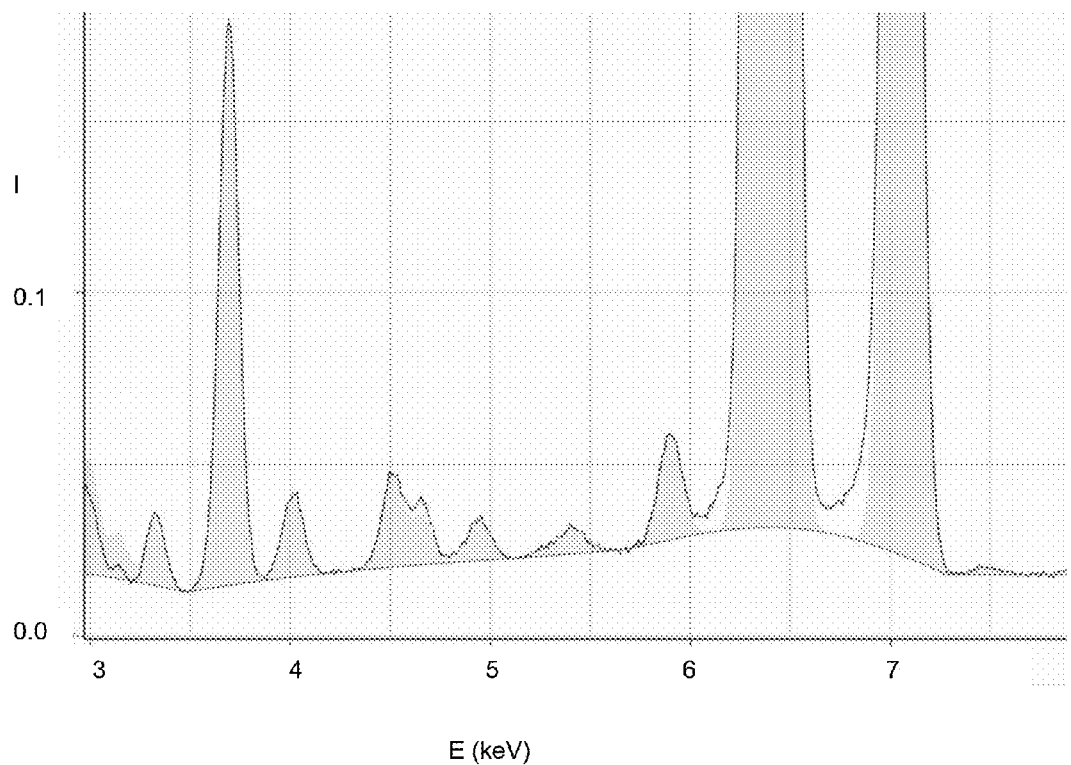
FIG. 2 shows a typical ED Spectrum obtained using the apparatus of FIG. 1.

FIG. 2 illustrates part of a spectrum as measured using 25 kV, 160 mA and 200 s. The shaded areas give the amounts of each element.

For each element, a calibration line linking the amount of the element in % and the intensity may be obtained using samples having a range of different percentages of the oxides concerned. The sensitivity S is the intensity signal for each % of the element in the sample and may be represented in kcps/% (thousand counts per second per %) from the calibration line relating intensity to % of the material. The slope of the calibration line is the reciprocal of the sensitivity, and will be referred to as E (=1/S).

These calibration parameters lead to the conclusion that WD-XRF might be used for most of the required elements, and that ED-XRF might be used for Si, Ca, and higher atomic numbers.

However, such factors fail to take fully into account repeatability of measurements which is of course important in many applications. In particular, the lower sensitivity of ED-XRF results in less repeatability at the low end of a calibration (small quantity of element).

For the condition that the peak from the element is much higher than the background, the condition for the precision and accuracy of the results to be obtained from ED-XRF to be (approximately) as good as or better than obtained from WD-XRF is given by:

$$\frac{E_{ED}}{E_{WD}} \leq \frac{t_{ED}}{t_{WD}} \quad (1)$$

where E is the reciprocal of the sensitivity, $E_{ED}$ is the reciprocal sensitivity for ED-XRF, $E_{WD}$ is the reciprocal sensitivity for WD-XRF, $t_{ED}$ is the measurement time for the ED-XRF measurements and $t_{WD}$ is the measurement time for the WD-XRF measurement.

In other words, if the ED-XRF measurement has half the sensitivity, the value of E is double, and the time taken needs to be double.

Thus, the total measurement time is reduced using condition 1 to determine whether any individual measurement at a particular energy corresponding to a particular element may be obtained by from the general ED-XRF measurement instead of a specific WD-XRF measurement for that energy. Those skilled in the art can calculate how to divide up the measurements to minimise the total measurement time based on this condition—for example if the time for an ED-XRF measurement is doubled this may mean that more elements can be measured by that ED-XRF measurement to required accuracy than by WD-XRF, according to equation (1), and a computer can readily calculate the total time and hence determine whether doubling the time for ED-XRF measurement increases or decreases the total measurement time.

Note that when determining which elements to measure using WD-XRF and which ED-XRF it should be remembered that the WD measurements require a separate measurement for each element and also for each background position measured while the ED measurement can measure multiple elements and background positions simultaneously.

In general, this approach allows for the optimisation (reduction) of total measurement time.

For the opposite condition, where the background radiation at the energy of the peak is as big as the peak signal or larger, then the condition is more complex:

$$E_{WD}\sqrt{\frac{r_{peak}}{t_{peak}} + l_{bkg1}^2 \frac{r_{bkg1}}{t_{bkg1}} + l_{bkg2}^2 \frac{r_{bkg2}}{t_{bkg2}} + \ldots} \geq \quad (2)$$

$$E_{ED}\sqrt{\frac{1}{LT} \cdot \left(\frac{r_{peak}}{t_{ED}} + \frac{r_{bkg}}{t_{ED}}\right)}$$

where $r_{peak}$ is the count rate at the peak position, $t_{peak}$ is the measurement time of the peak, $r_{bkg1}$ is the count rate at a $1^{st}$ background position, $t_{bkg1}$ is the corresponding measurement time, $l_{bkg1}$ is the corresponding background factor, with the same for other background positions 2, 3 . . . , LT is the Live Time of the ED channel in relative units, $r_{peak}$ the count rate at the peak position, and $t_{ED}$ is the measurement time of the ED channel.

The background is measured by taking a measurement away from all peaks. In some cases, there is only one background measurement but in other cases there may be more than one measurement. The background factors for the background sum to 1 and ensure that the background is correctly counted regardless of whether there is one or multiple background measurements. If only one background measurement is taken, then $l_{bkg1}=1$. If two background measurements are taken, then if they are both equidistant from the peak of interest then $l_{bkg1}=l_{bkg2}=0.5$. If the second measurement is further from the peak of interest (in terms of 2θ for WD-XRF measurements) then it will have a lower background factor. The background factors are inversely proportional to the distance to the peak, so if the second background measurement is twice as far from the peak as the first background measurement is from the peak the second background factor will be half the background factor of the first background measurement: $l_{bkg1}=\frac{2}{3}$ 1 and $l_{bkg2}==\frac{1}{3}$.

To explain the parameter LT further, note that ED detectors cannot in general measure continuously. If an ED detector can only measure for 50% of the time and is dead for the other 50% of the time (because there is a pile up of photons: the next photon is arriving before the earlier photon is processed, both are thrown away and the detector is dead, ie cannot detect new photons during that time), the factor LT is 0.5. In other words, this factor LT is the proportion of the total measurement time $t_{ED}$ required for measurement that the ED detector is receiving detected intensity.

The count rate in these formulae are a measure of intensity suitable for any detector. Other suitable intensity measures may equivalently be used if appropriate.

Using these equations, it is possible to determine for which elements the WD-XRF can be replaced with ED-XRF without sacrificing significant accuracy, repeatability or precision, and to reduce or minimise accordingly the total measurement time.

This leads to the following measurement program times. Note that the times according to the invention are provided in the "WD-ED" column and the "Classic WD" times are those of a comparative example where all elements are measured with WD-XRF.

TABLE 3

|  | Classic WD | WD + ED |
|---|---|---|
| 32 kV/125 mA, no filter | | |
| Na2O | 36 | 36 |
| MgO | 40 | 40 |
| Al2O3 | 74 | 74 |
| P2O5 | 24 | 24 |
| SO3 | 24 | 24 |
| K2O | 52 | 52 |
| CaO | 116 | 116 |
| Cr2O3 | 16 | 16 |
| TiO2 | 18 | |
| Mn3O4 | 44 | |
| SiO2 | 16 | |
| Fe2O3 | 20 | (500 s) |
| V2O5 | 22 | |
| ZnO | 14 | |
| As2O3 | 16 | |
| 60 kV/66 mA, Al-750 | | |
| NiO | 92 | 92 |
| PbO | 24 | 24 |
| CuO | 8 | (120 s) |
| Channel time | 656 | 498 |
| Overhead time | 197 | 149 |

Thus, in this example Ti, Mn, Si, Fe, V, Zn, As and Cu are measured using ED-XRF and the remaining elements with WD-XRF.

By selecting the appropriate elements to measure, the total time to measure the comparative example is 853 s (14 minutes 13 s) and for the WD-ED method according to the invention 647 s (10 minutes 47 s), about 24% less.

The measured results fall well within the expected accuracy of standard CRM-676-1.

The above example is for the measurement of Iron Ore. However, the same approach may be used in other applications.

By using equations (1) and (2) above it is possible to select which WD-XRF measurements can be replaced by ED-XRF measurements without resulting in significant reduction in accuracy.

Note that equation (2) in particular takes account of the effects of neighbouring peaks in the measurement since each such peak represents a separate contribution to the "Background" in equation (2). Thus, by using this approach accurate assessment of which approach is best is possible. Note for example that Si can be measured by ED-XRF even though it is a low Z element and might have been thought to be more suitable for WD-XRF if a simplistic view was taken of simply using WD-XRF for low Z elements and ED-XRF for high Z elements.

Further considerations may be taken into account to further enhance the measurement and improve selection of elements for WD and elements for ED.

One additional consideration is background correction, i.e. the intensity that does not arrive from a measurement of the peak in question or of neighbouring peaks but from the background. Background correction involves determining a general level of background, perhaps by measuring a signal at a range of close energies, and then subtracting the background signal from the signal measured at the energy of interest to obtain a background corrected signal.

Note that the ED-XRF measurements do not merely measure the intensity at the peaks of interest but also at the background locations all at the same time. Thus, ED-XRF measurements may be faster where the need to correct for background is important.

Another consideration is a matrix correction, i.e. the effects of other components in the sample on the measured X-ray fluorescence intensity. Such effects can also be taken into consideration. In this case, the ED-XRF measurements may be used to obtain a first approximation to the composition of the sample, i.e. the concentration of various components in the sample, and this information used to carry out a matrix correction on the measured intensity for all or some of the elements measured by WD-XRF as well as ED-XRF. In this context, carrying out a matrix correction means correcting the measured intensity for the effects of other components in the sample.

The inventors have also evaluated the method for geologic samples with similar results.

The optimal instrument settings for the ED-XRF measurements may differ from the WD-XRF measurements. In particular, since the X-ray detector for the WD-XRF measurements is behind an analyser crystal, the quantity of X-rays reaching the ED-XRF detector can be much higher than the quantity of X-rays reaching the X-ray detectors for WD-XRF. This can result in saturation of the ED-XRF detectors for a source power and current that only provides a small amount of signal in WD-XRF.

For this reason, the ED-XRF channel may include a double pinhole collimator 52,54 with a plurality of settings. These can include one or more settings which simply act as a collimator and one or more settings which reduce the area of the sample being measured. More than one setting as a collimator may provide a plurality of different reductions in intensity to reduce the X-ray intensity at the ED-XRF detector to sensible levels.

For WD-XRF, the typical size of the X-ray spot measured on the sample may be a diameter of 27 mm or 37 mm. The small spot settings can reduce the detected spot size for the ED-XRF, for example to 20 mm, 10 mm or even less. It may in particular be possible to reduce the effective spot size for ED-XRF to as low as 2 mm, or further to 0.5 mm or even 0.1 mm. This can provide optimal measurements for both ED and WD.

It may be possible to carry out both WD-XRF and ED-XRF measurements simultaneously. This can speed up processing.

Alternatively, if it results in a faster overall measurement, in some cases it may be faster to carry out optimised ED-XRF and WD-XRF one after the other, if the increase in speed by optimising each measurement separately is more significant than the reduction in time by carrying out some measurements simultaneously.

A further approach that may be useful in some cases is to dynamically select the elements to be measured by WD-XRF on the basis of the ED-XRF measurements. In this case, an initial ED-XRF measurement is made and on the basis of these measurements suitable elements are measured with WD-XRF. For example, if the initial ED-XRF measurement detects a trace element but the time for the ED-XRF measurement is too short for a suitable accuracy, this can be determined by the controller and that element may then be measured using WD-XRF. If the ED-XRF measurement does not detect the trace element in question, there is no need for the accurate measurement of that element by WD-XRF so the measurement of that element by WD-XRF can be omitted.

It should be noted that it may also be appropriate to consider the need for background measurements, i.e. measurements not at a specific line of interest, in a similar way. These too should be factored in to the timings for making measurements, and in particular to consider the need for these measurements. For example, it may be necessary not merely to measure an elemental line by WD-XRF but also to make a background measurement at a neighbouring position away from the peak and hence double the measurement time. As discussed above with regard to matrix correction, this is less of an issue for ED-XRF in which it is possible to measure both the intensity at the line and the background in the same measurement.

Those skilled in the art will realise that the same dynamic selection of WD-XRF measurements may apply in other circumstances. For example, if an initial ED-XRF measurement detects two close peaks, it may be necessary to measure both peaks by WD-XRF to obtain sufficient accuracy in the measurement of either or both peaks. In this case, as in the case of the previous paragraph, the selection of which measurements are made by WD-XRF is not predetermined but determined on the basis of the ED-XRF measurements.

This provision can also be reversed and ED-XRF measurements determined on the basis of WD-XRF.

Figure 3:
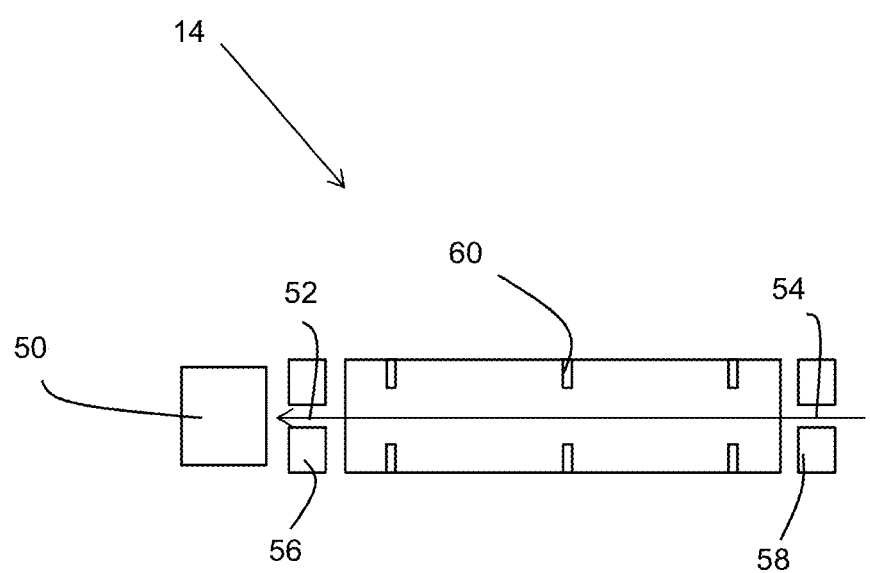
FIG. 3 shows an energy dispersive X-ray detector.

FIG. 3 illustrates the ED-XRF detector 14 with a silicon drift detector 50 and a double pinhole collimator including two pinholes 52, 54 each in an exchangeable element 56, 58 to enable the different intensity reductions/spot sizes to be selected by switching in and out appropriately sized pinholes. FIG. 3 also illustrates anti-scatter diaphragms 60 between the pin-holes which are provided to reduce the effects of any scattering between the pinholes.

Further means to reduce the intensity for ED-XRF can include an optional filter 62 in the path to reduce the intensity of radiation reaching the detector 14.

Figure 4:
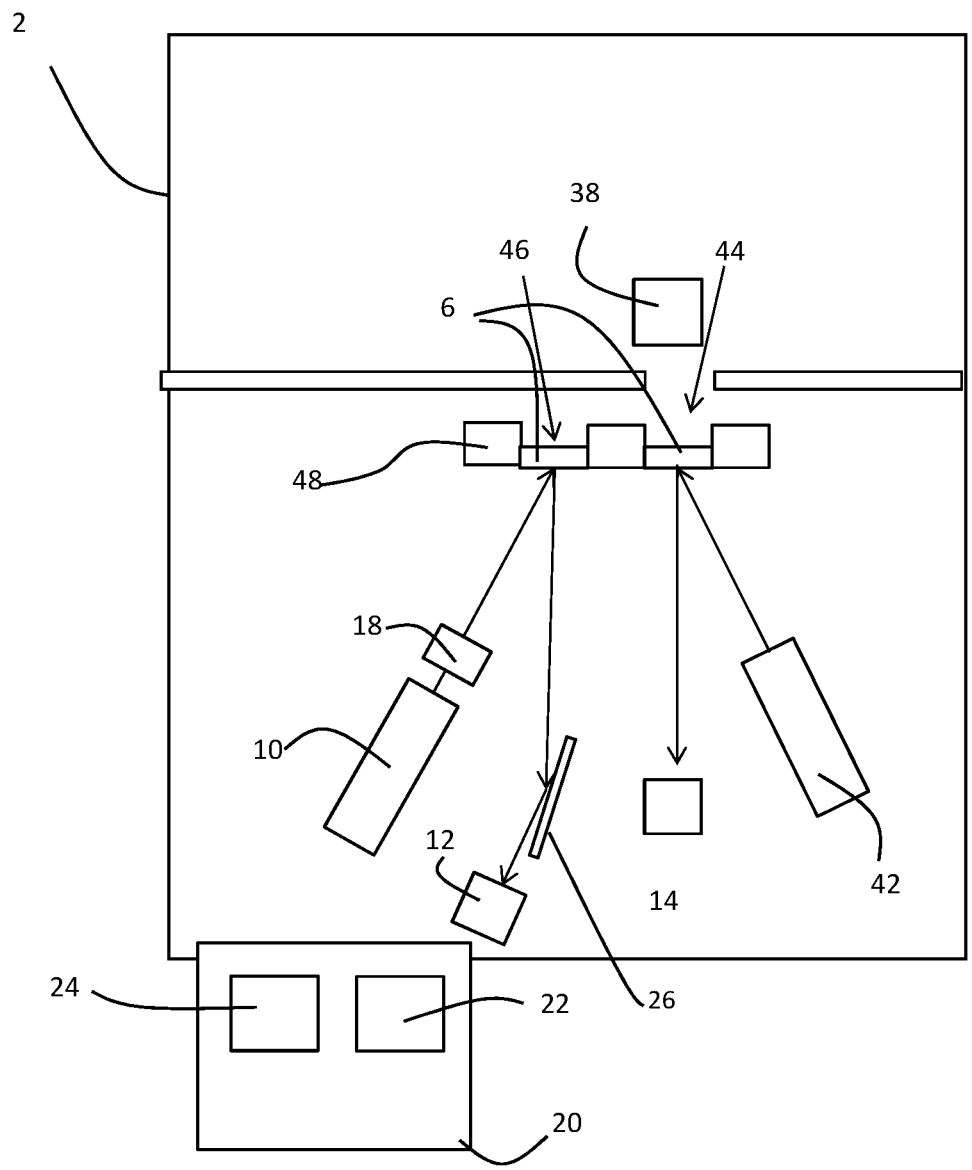
FIG. 4 shows a schematic of apparatus according to a second embodiment of the invention.

In a second embodiment, illustrated in FIG. 4 two different measurement positions 44, 46 are provided, a first measurement position 44 for ED-XRF and a second measurement position 46 for WD-XRF. Note that the sample 6 is loaded into the first measurement position 44 onto a rotary stage 48 and then rotated into second measurement position 46. The rotary stage 48 can mount two samples 6 simultaneously, one in each position. A sample loader 38 is arranged to load samples onto the sample stage in the first measurement position.

In this case, the X-ray source used for ED-XRF measurements is a low power X-ray source 42, for example 9 W to 50 W which matches well to a silicon drift detector as ED-XRF detector 14, and the X-ray source 10 used for the WD-XRF measurements is a high voltage/high power X-ray source capable of 160 kV, which matches well to a Si—Li or Ge detector as WD-XRF detector 12.

A high voltage source will excite high atomic number elements better yielding better performance for such elements. In contrast, a low power source 42 is sufficient for ED-XRF since the detector 14 is easily saturated. Typical powers of high power sources 10 for WD-XRF may be 1 to 4 kW.

By providing two different measurement positions it is possible to speed up measurement since a first sample can be loaded and the ED-XRF measurement taken with the first sample in first measurement position 44. The rotary stage is then rotated so that the first sample is in the second measurement position 46. While the WD-XRF measurement is taken in this second measurement position 46 a second sample is loaded into the first measurement position and the ED-XRF measurement of the first sample taken. The rotary stage 48 can then be rotated again and the second sample has the WD-XRF measurement taken while the first sample is removed, a third sample loaded and the ED-XRF measurement of the third sample taken. In this way a higher throughput of samples can be achieved.

More than two positions are possible, for example two measurement positions, one load position and one unload position. While the measurements are done simultaneously at the two measurement positions, a sample may be loaded in the load position and a sample is unloaded in the unload position In a further variation of the method, the ED-XRF measurements are taken and then evaluated to determine which WD-XRF measurements are required.

One option is to make the standardless calibration using the ED-XRF measurements and then calculate instrument factors for the WD-XRF measurements from that. In other words, the quantitative measures of the WD-XRF measurements use data from the ED-XRF.

Further, the so-called "Matrix correction" of the ED-XRF measurements to correct the measurements for other components present in the sample may also be carried out on the basis of the ED-XRF measurements. The ED-XRF measurements are carried out which gives an estimate of the amount of each of the components of the sample, even if this estimate may not be accurate enough for all elements. However, these estimates may be used to calculate the effects of each of the elements on measures of other elements for the WD-XRF calculation.

In a similar way, line overlap calculations for WD-XRF measurements may be based on estimates of the composition of the sample from the ED-XRF measurement.

Note that in this case it is convenient to carry out the ED-XRF measurements first and then the WD-XRF measurements but as an alternative the measurements can be carried out in any order and then combined by calculation in controller 20 at a later time.

Those skilled in the art will realise that the above approaches may be varied if required.

For example, the pinhole collimator on the ED-XRF channel may be replaced by a conical collimator or a capillary lens.

In the case of a multiple-position sample stage, instead of rotation a linearly translating stage may be provided. The stage may have more than two sample locations, for example a first sample location for loading as well as the first and second measurement positions as described above. Further measurement positions may also be added if required, either for further X-ray measurements, either XRF or XRD, or alternatively for additional measurements such as near infrared measurements.

We claim:

1. A method of quantitative X-ray fluorescence, XRF, analysis of a sample of a specified type to measure the concentration of a plurality of elements in respective concentration ranges, the method comprising:
   carrying out energy dispersive XRF, ED-XRF, to measure the concentration of a selected first subset of the predetermined elements;
   carrying out wavelength dispersive XRF, WD-XRF, to measure the concentration of a selected second sub-set of the elements;
   wherein the elements are divided between the first and second subsets according to a criterion to deliver a reduced overall measurement time to measure all the plurality of elements to a predetermined precision, accuracy and/or Lower Limit of Detection, LLD, compared to a method using WD-XRF for all elements up to a predetermined atomic number and ED-XRF for all elements with a higher atomic number, wherein in the case that the peak from the element is much higher than the background, the condition for ED-XRF to be used instead of WD-XRF is given by:

$$\frac{E_{ED}}{E_{WD}} \leq \frac{t_{ED}}{t_{WD}} \quad (1)$$

where E is the reciprocal of the sensitivity, $E_{ED}$ is the reciprocal sensitivity for ED-XRF, $E_{WD}$ is the reciprocal sensitivity for WD-XRF, $t_{ED}$ is the measurement time for the ED-XRF measurements and $t_{WD}$ is the measurement time for the WD-XRF measurement and/or in the case that the peak from the element is not higher than the background the criterion is that ED-XRF is used instead of WD-XRF for elements for which:

$$E_{WD}\sqrt{\frac{r_{peak}}{t_{peak}} + l_{bkg1}^2 \frac{r_{blg1}}{t_{bkg1}} + l_{bkg2}^2 \frac{r_{bkg2}}{t_{bkg2}} + \ldots} \geq E_{ED}\sqrt{\frac{1}{LT} \cdot \left(\frac{r_{peak}}{t_{ED}} + \frac{r_{bkg}}{t_{ED}}\right)} \quad (2)$$

where $r_{peak}$ is the count rate at the peak position, $t_{peak}$ is the measurement time of the peak, $r_{bkg1}$ is the count rate at the 1$^{st}$ background position, $t_{bkg1}$ is the measurement time of background1, idem background position 2, LT is the Live Time of the ED channel in relative units, $r_{peak}$ the count rate at the peak position, $r_{bkg}$ is the count rate at the background position, and $t_{ED}$ is the measurement time of the ED channel.

2. A method according to claim 1, wherein the criterion uses the reciprocal sensitivity of measurement E of each element by ED-XRF and WD-XRF.

3. A method according to claim 1, comprising using the ED-XRF data to determine the concentration of elements in the sample to a first approximation; and
matrix correcting the at least some of the WD-XRF measurements using the elements determined using the ED-XRF data.

4. A method according to claim 1, further comprising carrying out the ED-XRF measurements at the same time as carrying out at least some of the WD-XRF measurements.

5. A method according to claim 1, further comprising carrying out the ED-XRF measurements and then subsequently carrying out the WD-XRF measurements.

6. A method according to claim 1, further comprising carrying out the energy dispersive XRF measurements with the sample in a first measurement position and carrying out the wavelength dispersive XRF measurements with the sample in a second position.

7. Apparatus for carrying out X-ray fluorescence analysis comprising
a sample stage for carrying a sample;
an X-ray source arranged to direct X-rays to a sample on the sample stage;
a wavelength dispersive X-ray sensor;
an analyser crystal, wherein the analyser crystal cooperates with the wavelength dispersive X-ray sensor to direct X-rays of a selected wavelength emitted by the sample on the sample stage to the wavelength dispersive X-ray detector for measurement; and
an energy-dispersive X-ray detector;
further comprising a controller adapted to cause the apparatus to carry out a method according to claim 1.

8. A method according to claim 2, wherein the criterion for each element further takes into account the overlaps of other peaks, the expected concentration ranges and/or backgrounds of the predetermined elements.

9. A method according to claim 4, comprising determining dynamically which elements are to be measured by WD-XRF on the basis of the measurement results obtained by ED-XRF.

10. A method according to claim 6, further comprising loading a sample onto the sample stage in the first position while carrying out the WD XRF measurements on another sample in the second position.

11. Apparatus according to claim 7 wherein the sample stage is a movable sample stage having a first measurement position and a second measurement position;
wherein the X-ray source is arranged to direct X-rays to a sample mounted on the sample stage in the second measurement position;
the wavelength dispersive X-ray detector and analyser crystal are arranged to measure X-rays emitted by the sample in the second measurement position;
the apparatus further comprising a second X-ray source, arranged to direct X-rays to a sample mounted on the sample stage in the first measurement position;
wherein the energy-dispersive X-ray detector is arranged to measure the intensity of X-rays emitted by a sample in the first measurement position.

12. Apparatus according to claim 7, further comprising a collimator between the sample stage and the energy-dispersive X-ray detector.

13. Apparatus according to claim 11 wherein the sample stage is a rotary sample stage arranged to rotate to bring the samples between the first and second measurement positions.

14. Apparatus according to claim 11, further comprising a sample loader arranged to load a sample onto the sample stage in the first measurement position.

15. Apparatus according to claim 11, wherein the second source is a low energy X-ray source having a power of 5 W to 100 W.

16. Apparatus according to claim 11, wherein the second source is a low energy X-ray source having a power of 9 W to 50 W.

17. Apparatus according to claim 12, wherein the collimator is a variable collimator with a plurality of settings, with at least one setting for reducing the intensity of X-ray radiation reaching the energy dispersive X-ray detector and at least one setting for reducing the detected spot size on the sample.

18. Apparatus according to claim 12, further comprising a filter of brass, Al, Ag, Cu or Be between the sample and the ED-XRF detector.

* * * * *